United States Patent [19]

Turteltaub et al.

[11] Patent Number: 5,366,721

[45] Date of Patent: * Nov. 22, 1994

[54] METHOD FOR DETECTION OF LONG-LIVED RADIOISOTOPES IN SMALL BIOCHEMICAL SAMPLES

[75] Inventors: Kenneth W. Turteltaub, Livermore; John S. Vogel, Union City; James S. Felton, Danville; Barton L. Gledhill, Alamo; Jay C. Davis, Livermore, all of Calif.

[73] Assignee: Regents of the University of California, Oakland, Calif.

[ * ] Notice: The portion of the term of this patent subsequent to May 11, 2010 has been disclaimed.

[21] Appl. No.: 699,385

[22] Filed: Apr. 26, 1991

Related U.S. Application Data

[63] Continuation-in-part of Ser. No. 553,080, Jul. 13, 1990, abandoned.

[51] Int. Cl.$^5$ .................. A61K 43/00; A61N 5/00; A61B 6/00
[52] U.S. Cl. ................... 424/1.11; 436/56; 600/3; 128/654; 128/659
[58] Field of Search ............ 424/1.1; 436/56; 128/645, 659

[56] References Cited

U.S. PATENT DOCUMENTS 5,209,919  5/1993  Turtletaub et al. .......... 424/1.1

OTHER PUBLICATIONS

Litherland, "Ultrasensitive Mass Spectrometry w/ Accelerators," Ann. Rev. Nucl. Puri. Sci. 1980, 30: 437–73.
Elmore, "Ultrasensitive Radisiotope, Stable–Isotope, & Trace–Element Analysis . . . ", Biological Trace Element Research, vol. 12, 1987, 231–244.
Felton et al., "Accelerator Mass Spectroscopy in the Biomedical Sciences . . . ", Paper Prepared for 5th International Conference on AMS, 10 May 1990.
Kerlson et al., "Possible Impact of the New Spectrometric techniques . . ." Proceedings of First Conference on Radiocarbon Dating w/ Accelerators, Apr. 20 & 21, 1978.
Vogel et al., "Application of AMS to the Biomedical Sciences," 5th International Conference on AMS, Paris, France, Apr. 23–27, 1990.
Turteltaub et al., "Accelerator Mass Spectroscopy in Biomedical Dosimetry: Relationship . . . ", Lawrence Livermore National Laboratory, Apr. 13, 1990.

*Primary Examiner*—Robert L. Stoll
*Assistant Examiner*—Lara E. Chapman
*Attorney, Agent, or Firm*—Daryl S. Grzybicki; Henry P. Sartorio

[57] ABSTRACT

Disclosed is a method for detection of long-lived radioisotopes in small bio-chemical samples, comprising:
  a. selecting a biological host in which radioisotopes are present in concentrations equal to or less than those in the ambient biosphere,
  b. preparing a long-lived radioisotope labeled reactive chemical specie,
  c. administering said chemical specie to said biologist host in doses sufficiently low to avoid significant overt damage to the biological system thereof,
  d. allowing a period of time to elapse sufficient for dissemination and interaction of said chemical specie with said host throughout said biological system of said host,
  e. isolating a reacted fraction of the biological substance from said host in a manner sufficient to avoid contamination of said substance from extraneous sources,
  f. converting said fraction of biological substance by suitable means to a material which efficiently produces charged ions in at least one of several possible ion sources without introduction of significant isotopic fractionation, and,
  g. measuring the radioisotope concentration in said material by means of direct isotopic counting.

2 Claims, 3 Drawing Sheets

METHOD FOR DETECTION OF LONG-LIVED RADIOISOTOPES IN SMALL BIOCHEMICAL SAMPLES

The United States Government has rights in this invention pursuant to Contract No. W-7405-ENG-48 between the United States Department of Energy and the University of California for the operation of Lawrence Livermore National Laboratory.

RELATED APPLICATIONS

This application is a continuation-in-part of the application Ser. No. 553,080, filed Jul. 13, 1990, now abandoned by the same inventors, hereby incorporated by reference herein.

BACKGROUND OF THE INVENTION

1. Field of the Invention

The present invention relates to a method of measurement in biological systems and biochemical samples. More particularly, it relates to a method of quantifying molecular mixtures of and adhesions to minute amounts of biological substances or biochemical samples using an accelerator mass spectrometer. Still more particularly, it relates to a method of measurement using intermediate and long-lived radioisotopes bound to small biological substances or biochemical samples which are then converted to forms suitable for analysis by direct isotopic counting using accelerator mass spectrometry.

2. Background of the Invention

Isotopes of various elements have been used in biological processes for some time as a means of tracing, to determine fate and speeds of reaction processes, and for other purposes.

The measurements are made by scintillation counters, autoradiography or other devices which measure the amount of decay of isotopes which have a relatively short half life.

These methods, in general, cannot be used where human beings are involved because of the potential radiation damage from the isotopes and the amount of sample required. At radiation levels which are not harmful to humans, decay counting methods are insufficiently specific and sensitive to give meaningful results. Moreover, the background contamination is high, creating problems for the users of the equipment.

THE PRIOR ART

A suggested solution of overcoming the problems associated with the use of short half life isotopes is to use an accelerator mass spectrometer.

As described by D. Elmore in an article in Biological Trace Element Research, Vol. 12, 1987, accelerator mass spectrometers can be used for a variety of purposes using long-lived radioisotopes. Such purposes include the introduction of isotopes as tracers, then chemically processing the bulk tissue samples.

U.S. Pat. No. 4,037,100 describes an apparatus which can be used for the detection of electronegative particles and to provide data as to their elemental composition. The apparatus includes an accelerator mass spectrometer (AMS) which can be used for making mass and elemental analyses. Still other references to AMS devices, and their uses include: Kilius et al., "Separation of $^{26}$AL and $^{26}$Mg Isobars by Negative Ion Mass Spectrometry," Nature, Vol. 282, November 1979; A. E. Litherland, "Acceleration Mass Spectrometry," Nuclear Instruments and Methods in Physics Research B5, pp. 100–108, (1984); L. Brown, "Applications of Accelerator Mass Spectrometry," Ann. Rev. Earth Planet. Sci., vol. 12, pp. 39–59, (1984); and A. E. Litherland, "Ultrasensitive Mass Spectrometry with Accelerators," Ann. Rev. Nucl. Part. Sci., vol. 30, pp. 437–473, (1980).

Accelerator mass spectrometry (AMS) was developed as a highly sensitive method for counting long-lived but rare cosmogenic isotopes, typically those having half-lives between $10^3$ and $2 \times 10^7$ years. Isotopes with this range of half-lives are too long-lived to detect easily by conventional decay counting techniques but are too short-lived on geological timescales to be present in appreciable concentrations in the biosphere or lithosphere. Assay of these cosmogenic isotopes ($^{10}$Be, $^{14}$C, $^{26}$Al, $^{41}$Ca, $^{36}$Cl, and $^{129}$I) by AMS has become a fundamental tool in archaeology, oceanography, and the geosciences, but has not been applied to problems of a biological or clinical nature.

The ability of accelerator mass spectrometry (AMS) to measure concentrations of rare isotopes in 20 $\mu$g to 1-mg samples suggests that its extension to the biomedical sciences is a natural and potentially powerful application of the technology. The great enhancement in $^{14}$C detection sensitivity available with AMS offers the distinct advantage of detecting extremely small amounts of covalently bound $^{14}$C-labeled carcinogens to DNA with known stoichiometry over a wide range of carcinogen binding.

Historically, measurement of isotopically tagged materials has been avoided by AMS laboratories due, at least in part, to concerns over facility contamination. Measurements on biological materials have shown that contamination of AMS instrumentation by samples prepared in biomedical laboratories with a history of $^{14}$C usage is indeed a problem. In an effort to make this technology available to the biomedical and environmental sciences communities, sample handling methods described herein have been invented to overcome such gross contamination.

The present invention makes possible the measurement of long-lived radioisotopes in small amounts of specifically isolated and characterized biochemicals. Whereas radioisotopes are commonly detected in biochemicals, and whereas very specific means have been demonstrated for the isolation of small amounts of biochemicals, the amounts of purified biochemicals have been too small for use in quantification of long-lived isotopes by decay counting techniques. Instead, as previously mentioned, short-lived isotopes have been detected in scintillation and other decay-related detector systems for small, isolated biochemical fractions; or long-lived isotopes were detected in large quantities of less specific samples. Both of these approaches sacrifice information which is valuable in understanding biological systems at the molecular level. Short-lived isotopes cannot be used over long periods of time without normalization for the rate of decay, and are not suitable for the study of long term effects in a biological system nor for comparison between biological systems which are studied sequentially.

Further, the manufacture of compounds containing short-lived isotopes requires that the isotope be inserted only a short time before the compound is to be used in a radio-tracer experiment. In order to make such manufacture feasible, it is often necessary to attach the radioisotope to the exterior part of the molecule, in a bonding structure which is not stable against loss of the attached isotope. The ease in making such radio-chemicals is offset by the ease of losing the radioisotope from the labeled molecule. The isotope then becomes a source of experimental contamination if it becomes attached to part of the apparatus or becomes an impediment to sensitive measurements if it becomes attached to other molecules in the biological system being studied. Further, such isotopes undergo rapid decay not only in the scintillation or other decay-related counter, but they also deposit radiation and its concommittant energy into the prepared radio-chemical or into the biological host during after the experiment. The radiation can be damaging to the biological system under study as well as to experimenters and technicians handling the materials.

Long-lived radioisotopes eliminate many of these deficiencies. Isotopes whose lifetimes are long compared to the span of time in which the isotope is to be detected, either in a single biological system or in a series of different systems, eliminate the need for normalization of results before comparison. The manufacture of the compound which contains the isotope can be separated from the use of the compound, both in space and in time. Isotopes of elements which are most rigidly bound within the chemical compound can be chosen as labels, even if the manufacture of the compound is complex. Further, strongly bound isotopes, no matter what their decay properties, can be used to eliminate accidental loss of the label and the introduction of contamination of the biological system or the experimental apparatus. For example, radio-carbon ($14_C$) is one such long-lived isotope which can be introduced into stable parts of biochemicals. Finally, long-lived isotopes do not pose radiation hazards to the biological system under study nor to the handlers.

There are presently many techniques which can be used to separate biochemicals from mixtures of chemicals or biological systems which contain many different molecules. These techniques provide quantified, separated, or isolated biochemicals which can be used to understand biological systems at the level of molecular interactions. This invention makes possible the combination of the benefits of specific biochemical analysis and the detection through accelerator mass spectrometry of compounds which are labeled with long-lived isotopes.

It is an object of this invention to provide a method of biological analyses which is more specific than prior art methods.

It is a further object of this invention to provide a method of quantitive biological analysis which is order of magnitude more sensitive than methods known heretofore.

It is a still further object of this invention to provide a method of quantifying molecular mixtures of and adhesions to minute amounts of biological substances.

It is yet another object of this invention to provide a method of quantitive biological analysis using rare stable isotopes.

Still another object of the invention is to provide a method of measuring the concentrations of long-lived radioisotopes at levels of a few parts in $10^{15}$ to parts in $10^8$ which can signal the presence or effects of very small amounts of labeled exogenous biochemicals within biological systems, organs, fluids, cells or parts of cells of living hosts, including humans.

Yet another object of the invention is to provide a method of measuring the concentrations of long-lived radioisotopes from within biological systems which does not make use of the radioactive decay of these isotopes.

A still further object of the invention is to provide a method of quantifying the amount of an exogenous biochemical or several parts of an exogenous biochemical which have become adhered to or mixed with the natural biochemicals of a biological system using long-lived, radioactive molecular labels which are too low in concentration to be detected using techniques which depend on the decay of the radioisotopes.

Another object of the invention is to provide a method of measuring the concentrations of long-lived radioisotopes from within biological systems in which the labeled exogenous biochemical is stable over periods of time which are long compared to the period of biological effectiveness.

Another object of the invention is to provide a method of measuring the concentrations of long-lived radioisotopes from within biological systems in which the labeled exogenous biochemical is a close analogue of the natural, unlabeled form of the biochemical and without resort to tile substitution of elements within the biochemical by short-lived radioisotopes of other similar elements or chemically labile short-lived radioisotopes.

Still another object of the invention is to provide a method to measure the concentration of long-lived radioisotopes from within biological systems which represent molecular events whose probability is so low that natural levels of radioisotopes would mask the radioisotope labels attached to the exogenous effector.

These and other objects of the invention will be realized in the description, drawings, and claims to follow.

SUMMARY OF THE INVENTION

The invention consists of a method wherein a useful measurement of molecular mixtures or biochemical reaction products is obtained. It also consists of procedures and processes which make possible the measurement of long-lived radioisotopes in small amounts of quantified biological substances.

As used herein, the term "biological substance" refers to terrestrial and marine plant and animal substances.

The method of the invention comprises the following steps:

a. selecting a biological host in which radioisotopes are present in concentrations equal to or less than those in the ambient biosphere, b. preparing a long-lived radioisotope labeled reactive chemical specie, c. administering said chemical specie to said biological host in doses sufficiently low to avoid significant overt damage to the biological system thereof, d. allowing a period of time to elapse sufficient for dissemination and interaction of said chemical specie with said host throughout said biological system of said host, e. isolating a reacted fraction of the biological substance from said host in a manner sufficient to avoid contamination of said substance from extraneous sources, f. converting said fraction of biological substance by suitable means to a material which efficiently produces charged ions in at least one of several possible ion sources without introduction of significant isotopic fractionation, and, g. measuring the radioisotope concentration in said material by means of direct isotopic counting.

DETAILED DESCRIPTION OF THE INVENTION

The method embodying this invention includes producing or identifying biological systems or hosts which have low concentrations of the radioisotope to be used in quantifying a biological interaction, whether the low isotope concentration results from natural processes or through specific preparation or growth. This low concentration is identified by isolation and measurement of parts of the biological system or similar hosts through application of the further processes of this invention.

Compounds to be traced using the method of this invention are prepared with one or more long-lived radioisotopes incorporated into stably bonded locations of the molecules. These compounds are produced at or are diluted to radioisotope concentrations which do not provide significant increases in radiological exposure over the ambient radiation environment. The dilutions are performed successively in clean, new, disposable containers using clean, new, disposable pipettes. The biological hosts or systems are dosed with the compounds in order of their radioisotope content, lowest to highest. The locations of handling the labeled compounds and the biological substances, which are investigated, are prepared by determining the contamination levels present, by isolation of the surfaces to be worked on, by judicious use of disposable coverings and laboratory ware, and by ordered arrangement of the dosed materials. The biochemical substances to be finally analyzed for isotopic content are separated and purified using techniques which prevent cross contamination. The equipment to be used is disposable insofar as it comes in contact with any of the sampled materials or substances. The separated biochemicals are prepared for isotopic measurement by dilution to concentrations compatible with mass spectrometry equipment. The materials are then converted to solid, inert, non-volatile, thermally conductive compounds without modification of the isotopic concentrations.

In the example of radiocarbon ($^{14}C$) as a tracer, the process of combustion and graphitization can be used as enabled in: J. S. Vogel, J. R. Southon, D. E. Nelson, and T. A. Brown; 1984, Performance of catalytically condensed carbon for use in AMS, Nucl. Inst. and Meth., v, B5, p. 289-293 and J. S. Vogel, D. E. Nelson, and J. R. Southon; 1987, Radiocarbon background levels in an AMS system, Radiocarbon, v. 29, p. 323-333. Other methods such as are disclosed in Example 2, infra, may be used in the preparation of samples for analysis of isotopes other than those of carbon, more specifically, the isotopes of hydrogen. The prepared biomedical samples are then measured in an accelerator mass spectrometer with comparison to materials having known standard isotope concentrations. The isotope concentrations of the original biological substances are determined by normalization to the standards and correction for the dilutions and any measured introduced contaminations.

Figure 5:
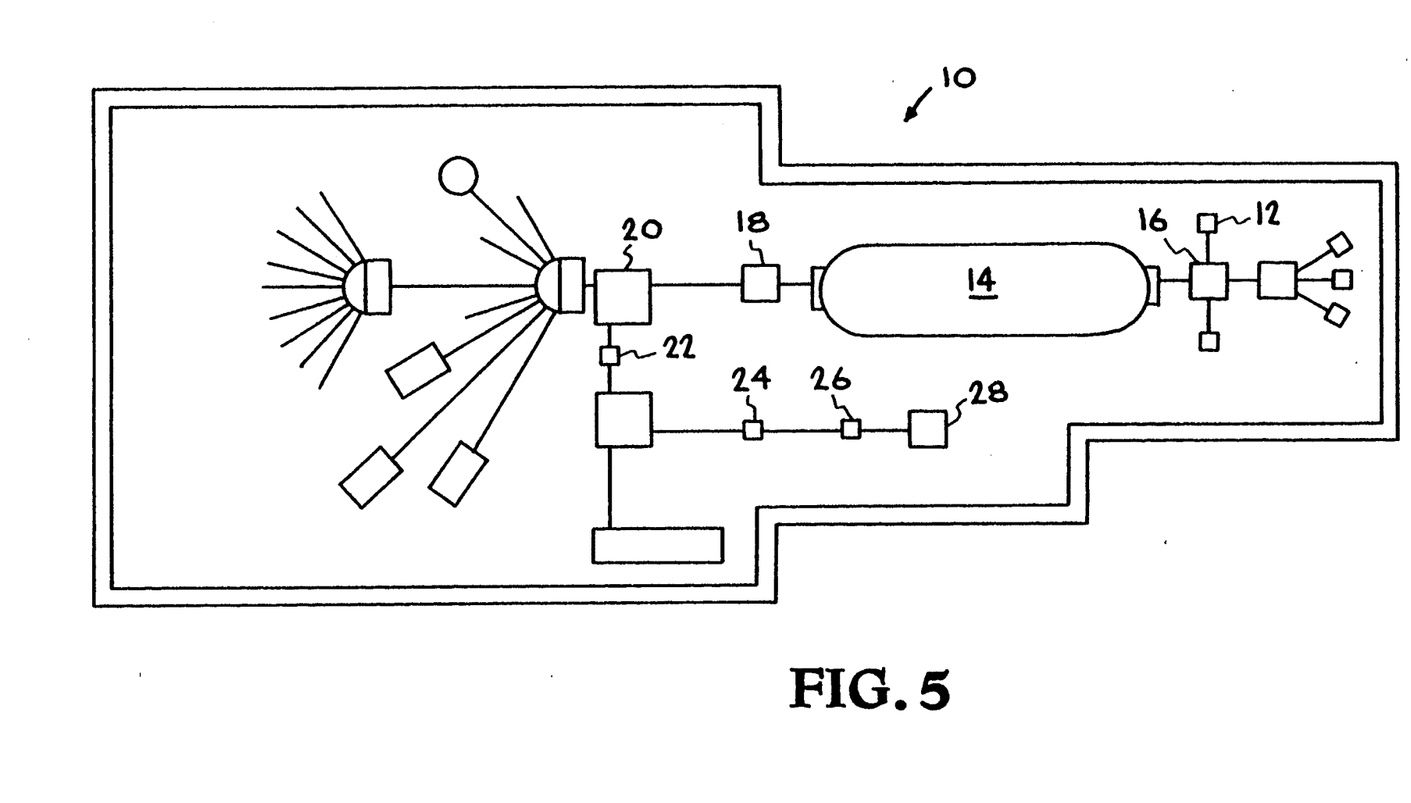
FIG. 5: Is a schematic drawing of accelerator mass spectrometry apparatus used in carrying out the method of the invention.

The method of the invention is carried out with the use of an accelerator mass spectrometer (AMS). Such devices can be purchased on the open market, but the specific one used to carry out the procedures described in the examples below was custom built at Lawrence Livermore National Laboratory. It is shown in FIG. 5 and is described as follows:

Beam Optics Design

The spectrometer 10 was designed using the beam optics code OPTRYK. An important design aim was to achieve high sample throughput through use of a high intensity multi-sample ion source. Operation at high current raised the possibility of intensity-dependent beam losses in the system arising from space charge effects near the source. The system was therefore designed for the best possible beam transmission to minimize such effects. Other important considerations included ease of tuning and operation through provision of adequate beam diagnostics and corrective steerers, and computer control of the transport system to allow eventual unattended operation.

Ion Source and Injection

The AMS ion source 12 is a Genus Model 846 sputter source, equipped with a 60-sample changer. Operating voltages are 8 kV on the source cathode plus 25-30 kV on the extraction, for a total injection energy of just 35 kV. The decision was taken not to place the source on a high voltage deck, since the large calculated acceptance of the modified FN 14 indicated that beam transmission for typical sputter source emittances would be excellent, and the design of the injection beam line is simplified. Beams from the source are focussed by an einzel lens on to the object slits of a 90° double-focussing Danfysik injection magnet 16 (r=50 cm, ME/Z2=7.5). The magnet is provided with rotatable downstream pole tips so that a second ion source leg opposite the present one can be implemented. The vacuum box is insulated to +5 kV. By means of high voltage switches connecting the box to DC power supplies or to ground, different isotopes are switched into the accelerator under control of the data acquisition system. A large magnet gap of 5 cm was specified to ensure good transmission, and the accel-deccel gaps placed near the magnet object and image positions were also made large (10 cm diameter) to increase the lens focal lengths and thus minimize differential focussing for different bias voltages.

Accelerator

The FN accelerator 14 was obtained from the University of Washington, Seattle, and has been substantially upgraded. Dowlish titanium spiral inclined field accelerator tubes and a Felletron conversion were installed to increase the beam transmission and the terminal voltage range, and to improve energy stability and reliability. Although the entrance grid of the #1 Dowlish tube intercepts 10% of the injected beam, this loss is insensitive to changes in the beam size or position and so can be tolerated. The beam transmission with these tubes is otherwise excellent. Other improvements to the FN 14 included installation of a large (1 cm) diameter stripper canal and a turbomolecular terminal pump, for increased transmission with gas or foil strippers. Systems in the terminal are presently controlled via plastic rods, but an infrared light link control system can be used. The terminal voltage stabilization system currently relies on generating voltmeter and capacitive pickoff inputs, and voltage stabilities of about 1 part in $10^4$ are achieved.

The accelerator operating voltages were limited to 5.5 MV by the use of $N_2/CO_2$ insulating gas until the gas handling system had been thoroughly exercised and made leak-tight. The gas was recently replaced with $SF_6$ and the FN has been conditioned to 7.5 MV. The FN now operates uneventfully at 7 MV, so that optimum running conditions for the C4+charge state are attainable, and it is anticipated that further voltage increases to 10-11 MV will be routine.

High Energy Spectrometer

Scattering in the stripper in the accelerator terminal inevitably increases the emittance of the transmitted beam sufficiently to cause some losses in the high energy accelerator tubes, particularly for heavy isotopes and low energies. The high energy spectrometer was designed to pass the maximum beam divergence that could emerge from the Dowlish tubes to the AMS detectors without loss. This proved unexpectedly easy to accomplish using surplus large quadrupoles and analyzing magnets from LLNL and from the HEPL laboratory at Stanford University. A design consisting of two identical 90° magnets and a Wien filter was chosen for its good optical properties and compact layout.

Beams from the FN are focussed by a 10 cm diameter magnetic quadruple triplet 18 to the object point for the first analyzing magnet 20. The choice of magnetic quadruples is a compromise, since correct focussing is achieved for just one isotope at a time. The triplet misfocussing is accommodated by opening the object slits and was taken into account in the positioning of the Faraday Cups 22 which detect analyzed stable isotope beams. Since the analysis magnet gap is large, beam losses are avoided.

The two identical ex-HEPL dipoles (single-focussing, r=139 cm, gap=6.4 cm, ME/Z2=150) together form a first-order achromat, leading to a small beam waist at the start of the final beam line leg and reducing any jitter from energy shifts. The momentum dispersion at the image slits of the first magnet is about 1 in 800. Stable beams are detected in Faraday Cups 22 in a large vacuum chamber downstream of the magnet, and these cups are equipped with internal slits for beam position monitoring and for terminal voltage stabilization. The pole width is sufficiently wide that masses 12-14 could be accommodated without changing the magnet field, but this would require a new vacuum tank, and only $^{13}C$ and $^{14}C$ are accelerated at present.

The final beam line leg contains a second magnetic triplet 24, a Wien filter 26, and the AMS detectors 28. The Wien filter (length=1 m, gap=8 cm, 3 kG, 60 kV) was built by Danfysik and is a scaled up version of one used previously by the Simon Fraser AMS group, with a velocity resolution~v/v for 22.5 MeV $C^{4+}$ of about 1/120. The filter was preferred over electrostatic deflectors for the versatility provided by its variable dispersion and for the ease of alignment arising from the straight-line beam path. The optical magnification of the final leg was deliberately made large to provide a small final beam divergence. Longitudinal detector positions are less critical and time-of flight detectors of modest length can be implemented without using refocussing quadrupoles. Ample space is available to extend the line if long flight paths and refocussing prove to be necessary.

Data Acquisition

Particle detection is currently by means of a multi-anode transverse gas ionization detector. A longitudinal gas ionization detector for Be and two carbon foil channel plate time-of-flight detectors for heavy isotopes are also contemplated. Data acquisition is based on NIM and CAMAC electronics feeding CAMAC ADC's and scalers, with HP9000 workstations running under UNIX and in-house acquisition software written in C.

Control System

The accelerator and beam line elements are computer-controlled through CAMAC and HP9000 workstations, using a control system developed at LLNL and the CEBAF laboratory. Local computers each communicate via GPIB with a single CAMAC crate which controls a cluster of beam line elements. A supervisory computer at the operator console scans the local computers via a LAN, with a systemwide data update rake of about 10 Hz. The supervisor also controls the main graphics display, flags errors, and receives operator input through the keyboard or via 9 reassignable knobs. All definitions of signal connections and control algorithms are set up by manipulating icons with a graphics editor, so that control functions can be changed without writing new code.

The system controls the entire spectrometer, with the exceptions of the source sample changer, and the injection bounce timing which is driven by the data acquisition system.

This invention will be more fully understood by reference to the following examples, which are intended to be illustrative of the invention, but not limiting thereof.

EXAMPLE 1

Measurement of Recovered Antigens and Antibodies in a Radio-Immunoassay

The concentration of recovered antibodies and the concentration of recovered bound antigens are determined for a single sample from a radio-immunoassay by measuring the concentrations of both $^{14}C$ which is used to label the antigen and the $^3H$ which is used to label the binding antibodies in the same sample. Uniformly labeled 2,3,7,8-tetra-chloro-dibenzo-p-dioxin (TCDD) is obtained commercially containing all average of 11.7 $^{14}C$ atoms per molecule of TCDD. Antibodies specific to the binding of TCDD are produced by monoclonal techniques. An essential amino acid, such as cystine, is provided to the cloning process in a commercially-available, radioactively-labeled form, such as [$^3H$]Cys. Alternatively, the sulfur atoms in the cystine could be substituted by $^{79}Se$. The monoclonal antibodies are produced so that the labeled cystine is the sole source of cystine, which is required to make effective antibodies. For a specified immunoglobin, there is a specified amount of cystine and a concomitant specified amount of radioactive label in the antibody. In the usual manner of radio-immunoassays, the relation between the known concentration of labeled antigen and the fraction of that concentration which is bound to the antibodies for a fixed concentration of antibodies is found for a range of antigen concentrations which includes the expected antigen concentration to be assayed. The amount of the antigen bound to the antibody is usually found by radiometric determinations of the antigen's radioisotope label after the unbound fraction of the antigen has been separated from the bound antibody/antigens. The sensitivity of the usual immunoassay is limited by the requirement that sufficient, radioactivity be present in the bound fraction for radiometric counting after whatever process is used to separate the unbound fraction of antigen.

In this example, we measure the radioisotope concentration, and hence the bound antigen concentration, in the separated portions at sensitivities of $10^4$–$10^8$ molecules per micro-titer well by AMS techniques. The separation of bound antigen/antibody pairs from the solution containing unbound antigen or antibodies may be effected several ways and only one method is given here by way of example. The antibodies are fixed to very small glass beads, produced commercially for this purpose, and allowed to react with 100 $\mu$solutions of the antigen in wells of micro-titer plates. After suitable incubation, the unbound fractions of labeled antigen are removed with the remaining solute, the beads holding the antibodies and the bound antigen are recovered and further separated from unbound antigen by simple rinsing, preferably after application of a fixing agent to aid in the antigen binding as the chemical conditions change during processing.

The beads holding the separated bound antigen are vacuum dried and combusted in flowing oxygen or in sealed contact with solid oxidants such as cupric oxide at 700° C. The resultant $CO_2$ is collected and graphitized through catalytic reduction by hydrogen over cobalt or iron powder at 600° C. The resultant graphite is pressed into sample holders for a fast-ion-bombardment ion source and the resultant ions are measured against standard $^{14}$C-containing materials in an accelerator mass spectrometer.

For correct interpretation of the ratio of $^{14}$C to the total carbon in a sample, the amount of antibody present in the separated sample is accurately determined from the weight of the glass beads, or other such measure. Any uncertainty in the concentration of the antibodies which are recovered through separation and purification processes introduces uncertainty in the standard '% Bound' versus 'Antigen Concentration' curve. Alternatively, this uncertainty is eliminated by measuring the amount of antibody which is involved in the binding of the measured bound antigen by use of the second radioisotope label which has been incorporated into the antibodies during production. In this example, the water produced from the combustion of the beads holding the antibody and antigen is collected separately from the $CO_2$. The water contains the $^3$H which reflects the total amount of antibodies, bound and unbound, which are on the sample glass beads. The water is reduced against powdered Zn at 350°–400° C. in a closed volume and the resultant $H_2$ is absorbed into titanium powder at 480°–650° C. The resultant titanium hydride is pressed into the sample holders of a fast-ion-bombardment ion source and the resultant hydrogen ions are analyzed using accelerator mass spectrometry. The samples which are to be immunoassayed are then prepared and measured in the same manner as the samples used in making the response curve for the known antigen/antibody binding concentrations.

Alternatively to the individual preparation and measurement of the carbon and the hydrogen radioisotopes, the samples are reacted with strong Lewis acids, such as but not limited to aluminum bromide, which produces a material which can be used in the ion source and which contains both the carbon to be analyzed as well as the hydrogen to be analyzed. In this latter instance, the $^3$H and the $^{14}$C content are measured from the same sample during the same measurement, either by analyzing for the two isotopes simultaneously or alternately.

EXAMPLE 2

Preparation of Organic Biomedical Samples for AMS Determination of Radioisotope Content Samples of organic biochemicals, such as albumin, cellulose, sucrose, collagen, whole skin, sodium dodecyl sulfate and other ionic detergents, have been made into a thermally conductive and chemically inert uniform substrate for use in a fast-atom-bombardment ion source by interaction with molten Lewis acid salts. Milligram sized samples were placed in 6×50 mm borosilicate glass culture tubes. Liquid solutions of proteins and/or ionic detergents were pipetted into the tubes and the materials were vacuum dried. Solid samples such as collagen, skin or sucrose were placed directly into the tubes. Five to fifty milligram aliquots of the strong Lewis acid, anhydrous aluminum bromide, were added to the individual tubes. The tubes were placed within confinement vessels consisting of a 10×70 mm culture tube slipped within a 12×70 mm culture tube. The vessels containing the mixture of biochemical and aluminum bromide were then heated to over 100° C. but to less than 150° C. for 1 to 5 hours. The vessels and the reactants were heated in vacuum, air, or argon atmospheres. The Lewis acid transformed the biochemicals to a black, inert, uniform substance. After the reaction had finished, excess Lewis acid was driven out of the sample by heating to beyond the boiling point of the acid. In this example, the samples were heated to 300°–400° C., well above the 263.3° C. boiling point of aluminum bromide. The Lewis acid condensed on the cooler vessel surfaces above the sample. The 6×50 mm culture tubes containing the modified samples were removed from the vessels and hydrated aluminum bromide, which remained within the sample material, was removed by repeating rinsing with water. The sample material was vacuum dried to remove adsorbed gas. In order to increase the thermal conductivity of the material, metal powders were added to the samples either before the interaction with the Lewis acid, or after the vacuum drying of the prepared material. Metals tested for this purpose included, but are not restricted to, silver, titanium and cobalt. The use of titanium during the reaction with a strong Lewis acid promoted the inclusion of the hydrogen in the sample within the finished material. The finished material was pressed into sample holders which were placed in the cesium sputter source of the LLNL AMS facility. In order to reduce the thermal deposition into the sample, the ion source was operated at a relatively low cathode potential of 2.5–4 kV relative to the extraction potential. Negative carbon atom ion currents equal to 25 to 45% of those available from prepared filamentous graphite were extracted from the ion source. These ion beams were analyzed using normal AMS techniques.

Figure 1:
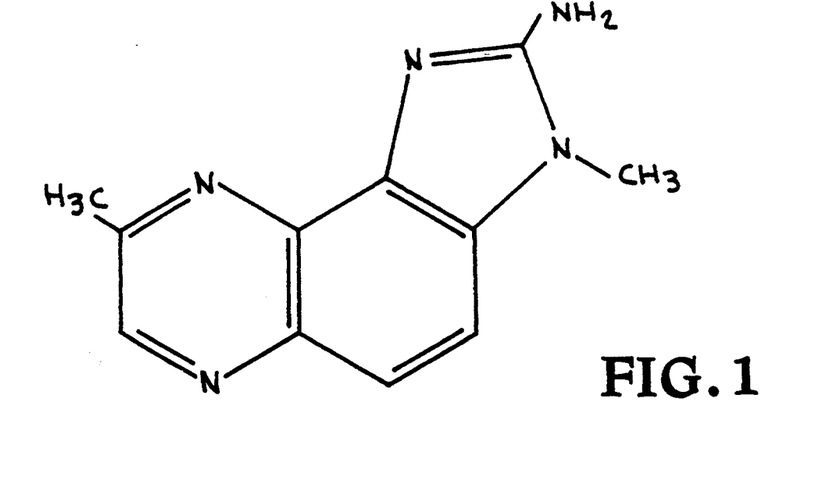
FIG. 1: Shows the structure of 2-amino-3,8-dimethlimidazo[4,5-f] quin-oxaline (MeIQx).

The method of this invention has been used to determine the relationship between carcinogen dose and DNA adduct levels in mice given very low levels of 2-amino-3,8-dimethylimidazo[4,5-f] quinoxaline (MeIQx; FIG. 1), a carcinogen found in cooked meat. This study illustrates the dynamic range, sensitivity and general applicability of AMS technology to problems in biomedical and environmental dosimetry, as well as presenting the relationship between DNA adducts and low-dose MeIQx exposure.

EXAMPLE 3

Detection of Amino-imidazoazaarene Adducts of DNA

The covalent binding of 2-amino-3,8-dimethylimidazo (4,5-F) quinoxaline (MeIQx), a carcinogen resulting from the cooking of meat, to murine hepatic deoxyribonucleic acids (DNA) was measured to a sensitivity of one DNA adduct per $10^{12}$ nucleotides. Eighteen (18) male C57BL/6 mice weighing 23–27 g were housed individually in new disposable polystyrene cages with hardwood bedding on a 12 hr light/dark cycle. Animals were fasted for 18 hr and then given single doses of [2-$^{14}$C]-MeIQx (50 mCi/mMol) which was synthesized (1) in the Lawrence Livermore Laboratory. New disposable syringes, gavage needles, and gloves worn by the technician were used for administration of the MeIQx to each animal. Each of the five dose levels were replicated 3 times. The radiopurity of the compound was greater than 97% as determined by high pressure liquid chromatography. Administration of the [$^{14}$C]-MeIQx was in corn oil by stomach intubation (0.1 ml volume). Doses of MeIQx were administered from 500 pg/kg to 5 mg/kg body weight. An additional set of 3 animals given only corn oil were used as controls. Animals were housed in ventilated negative air flow isolation units previously determined to be $^{14}$C-free by AMS and were sacrificed 24 hr after dosing by $CO_2$ asphyxiation.

Each animal was sacrificed and handled separately beginning with control animals in the order of increasing MeIQx dose. New dissection scissors and forceps were used on each animal and gloves were changed often to avoid cross-contamination of the tissues. Each dissection was carried out on freshly laid paper-covered laboratory benches and the paper covering was changed between each animal dissection. Livers were placed in individual disposable 50 ml centrifuge tubes, frozen on dry ice immediately following removal, taken to a separate laboratory, and the DNA was isolated as previously described (2) using freshly prepared solutions. Following DNA isolation, the DNA was dissolved in distilled water, extracted 3 times with aqueous 1-butanol, pH 8.0, and dialysed against sterile distilled water 3 times to insure removal of any residual non-covalently bound $^{14}$C. Samples were handled using disposable glassware in the order of increasing MeIQx dose. All equipment was used only once. Gloves were worn throughout the procedures and were changed between each sample.

The DNA was then diluted from 10 to 1000-fold with a 1 mg/ml sodium lauryl sulfate (SDS) solution which was previously determined to be 0.47 parts $^{14}$C in $10^{12}$. Approximately 0.5 mg of the DNA/SDS mixture was dried under vacuum in silica tubes, was combusted to $CO_2$ in sealed, evacuated tubes with CuO at 900° C. and reduced to filamentous graphite by hydrogen over a cobalt catalyst using a dedicated system built for handling labeled compounds as described by Vogel et al. (3,4). $^{14}$C free acrylamide and ANU sucrose standards (prepared by the Australian National University) were graphitized along with the samples to monitor for $^{14}$C carry-over. Water vapor degassing between preparations helped to remove residual $^{14}$C remaining in the instrumentation. The resultant graphite was pressed into individual, new sample holders for use in a cesium bombardment negative ion sputter source and the measurements were done using protocols developed for the AMS beamline at the Lawrence Livermore National Laboratory Multiuser Tandem Laboratory (5,6). ANU sucrose, with an activity 1.508 times the $^{14}$C activity of 1950 carbon, was used as analytical standard. Measurements are reported in units of Modern or as DNA adducts/$10^{12}$ nucleotides. Modern is defined as $5.9 \times 10^{10}$ 14C atoms per gram of carbon, and is approximately equal to the natural abundance of $^{14}$C present in contemporary (1950 A.D.) carbon (7). Determination of adduct levels is based on $^{14}$C measurement of the MeIQx DNA adduct. [$^{14}$C]-MeIQx binding was calculated by subtraction of the natural radiocarbon content from the measured $^{14}$C content of the samples. Adduct frequencies were normalized based on the assumption that 1 $\mu$g DNA=3240 pMol nucleotides. The lowest level of MeIQx DNA binding was detected at 1 adduct per $10^{11}$ deoxyribo-nucleotides and the number of 1 adducts per $10^{12}$ deoxynucleotides was linear with dose.

References

1. Grivas, S. (1985) Acta Chem. Scand. Ser. B. 39, 213–217.
2. Gupta, R. C. (1984) Proc. Natl. Acad. Sci., USA 81, 6943–6947.
3. Vogel, J. S., Nelson, D. E., and Southon, J. R. (1989) Radiocarbon 31, 145–149.
4. Vogel, J. S., Nelson, D. E., and Southon, J. R. (1987) Radiocarbon 29, 323–333.
5. Davis, J. C. (1989) Nucl. Instrum. Methods B40/41, 705–708.
6. Proctor, I. D. (1989) Nucl. Instrum. Methods B40/41, 727–730.
7. Stuiver, M., and Polach, H. A. (1977) Radiocarbon 19, 355–363.

EXAMPLE 4

Demonstration that 2,3,7,8-tetrachlorodibenzo-p-doxin does not Covalently Bind to DNA 2,3,7,8-tetrachloro-[U-$^{14}$C]dibenzo-p-dioxin (TCDD) was tested for its ability to covalently bind to murine hepatic deoxyribonucleic acids and thus for its potential to initiate mutagenesis at exposure concentrations well below the maximum tolerated dose and the lethal dose in this species. [U-$^{14}$C]TCDD, 122 mCi/mMol, >97% radiopurity by high pressure liquid chromatography, was purchased from Cambridge Isotope Laboratories (Woburn, Mass.). The TCDD was diluted in p-dioxane for administration to the mice. Eighteen (18) male C57BL/6 mice weighing 23–27 g were housed individually in new disposable polystyrene cages with hardwood bedding on a 12 hr light/dark cycle. Animals were fed ad Libitum. [U-$^{14}$C]TCDD was administered by intraperitonal injection (10 $\mu$l total volume). New disposable syringes, needles, and gloves worn by the technician were used for administration of the TCDD to each animals. Each of the five dose levels were replicated 3 times. Doses of TCDD were administered from 5 pg/kg to 100 pk/kg body weight. An additional set of 3 animals given only p-dioxane were used as controls. Animals were housed in ventilated negative air flow isolation units previously determined to be $^{14}$C-free by AMS and were sacrificed 24 hr after dosing by $CO_2$ asphyxiation.

Each animal was sacrificed and handled separately beginning with control animals in the order of increasing TCDD dose. New dissection scissors and forceps were used on each animal and gloves were changed frequently to avoid cross contamination of the tissues. Each dissection was carried out on freshly laid paper-covered laboratory benches and the paper covering was changed between each animal dissection. Livers were placed in individual disposable 50 ml centrifuge tubes, frozen on dry ice immediately following removal, taken to a separate laboratory, and the DNA isolated as previously described (1) using freshly prepared solutions. Following DNA isolation, the DNA was dissolved in distilled water, extracted 3 times with aqueous 1-butanol, pH 8.0, and dialysed against sterile distilled water 3 times to insure removal of any residual non-covalently bound $^{14}C$. Samples were handled using disposable glassware in the order of increasing TCDD dose. All equipment was used only once. Gloves were worn throughout the procedures and were changed between each sample. The DNA was then diluted from 10 to 1,000-fold with a 1 mg/ml sodium lauryl sulfate (SDS) solution which was previously determined to be 0.47 parts $^{14}C$ in $10^{12}$ total carbon. Approximately 0.5 mg of the DNA/SDS mixture was dried under vacuum in silica tubes, was combusted to $CO_2$ in sealed, evacuated tubes with CuO at 700° C. and reduced to filamentous graphite by hydrogen over a cobalt catalyst using a dedicated system built for handling labeled compounds as described by Vogel et al. (2,3). $^{14}C$-free acrylamide and ANU sucrose standards (prepared by the Australian National University) were graphitized along with the samples to monitor for $^{14}C$ carry-over. Water vapor degassing between preparations helped to remove residual $^{14}C$ remaining in the instrumentation. The resultant graphite was pressed into individual, new sample holders for use in a cesium bombardment negative ion sputter source and the measurements were done using protocols developed for the AMS beamline at the Lawrence Livermore National Laboratory Multiuser Tandem Laboratory (4,5). ANU sucrose, with an activity 1.508 times the $^{14}C$ activity of 1950 carbon, was used as analytical standard for the measurements. Measurements are reported in units of Modern or as DNA adducts/$10^{12}$ nucleotides. Modern is defined as $5.9 \times 10^{10}$ $^{14}C$ atoms/g carbon and is approximately equal to the natural abundance of $^{14}C$ present in contemporary (1950 A.D.) carbon (6). Determination of adduct levels is based on $^{14}C$ measurement of the TCDD-DNA adduct. [$^{14}C$]-TCDD binding was calculated by subtraction of the natural radiocarbon content from the measured $^{14}C$ content of the samples. Adduct frequencies were normalized based on the assumption that 1 μg DNA=3240 pMol deoxyribonucleotides.

The lowest level of TCDD DNA bonding was detected at the 100 μg/kg TCDD dose level and corresponded to measurement of 1 TCDD deoxyribonucleotide adduct per $10^{12}$ deoxyribonucleotides. This dose level is approximately equal to the TCDD L.D.$_{50}$ (murine L.D.$_{50}$=125 μg/kg) for this species demonstrating that TCDD does not bond to DNA below levels acutely toxic to the organism. DNA from all other dose levels contained only the natural abundance of $^{14}C$ (1 Modern). $^{14}C$ content at the highest TCDD dose level was 5000 times lower than that detected for an equivalent dose of $^{14}C$ from 2-amino 3,8-dimethyl [2-$^{14}C$]imidazo[4,5-f] quinaxaline treated mice demonstrating tile ability of this protocol to remove non-covalently bond $^{14}C$ from the samples.

References

1. Gupta, R. C. (1984) Proc. Nat 1. Acad. Sci., USA 81, 6943–6947.
2. Vogel, J. S., Nelson, D. E., and Southon, J. R. (1989) Radiocarbon 31, 145–149.
3. Vogel, J. S. Nelson, and Southon, J. R., (1987) Radiocarbon 29, 323–333.
4. Davis, J. C. (1989) Nucl. Instrum. Methods B40/41, 705–708.
5. Proctor, I. D. (1989) Nucl. Instrum. Methods B40/41, 727–730.
6. Stuiver, M., and Polach, H. A., (1977) Radiocarbon 19, 355–363.

EXAMPLE 5

Production and Measurement of $^{14}C$-Depleted Methanotrophic Bacteria

Growth of $^{14}C$ depleted bacteria was carried out to obtain a $^{14}C$-free biological host for low-dose toxicology studies. Methylosinus trichosporium Ob3b was obtained from Dr. R. Taylor (LLNL) and grown as described by Park et al. (1). Briefly, the bacteria were grown in a 5 bioreactor with continuous gas flow. Temperature was maintained at 30° C. at pH 6.8–7.2. The methane (petroleum-derived) flow rate was kept at 150–500 ml/hr. The flow rate for air containing 10% $CO_2$ was kept at 450–1500 ml/hr. Approximately 1 mg of bacteria (wet weight) was collected 7 days after infusion of methane and dried under vacuum. The bacterial sample was converted to elemental graphite and measured by combusted to $CO_2$ in sealed, evacuated tubes with CuO at 700° C. and reduced to filamentous graphite by hydrogen over a cobalt catalyst as described by Vogel et al. (2,3). $^{14}C$-free acrylamide was used to measure the processing background $^{14}C$ content. The resultant graphite was pressed into individual, new sample holders for use in a cesium bombardment negative ion sputter source and the measurements were done using protocols developed for the AMS beamline at the Lawrence Livermore National Laboratory Multiuser Tandem Laboratory (4,5). ANU sucrose, with an activity 1.508 times the $^{14}C$ activity of 1950 carbon, was used as analytical standard. The bacterial carbon contained $^{14}C$ at the same concentration as the acrylamide processing blank, and was two orders of magnitude lower than the normal $^{14}C$ content of living organisms at equilibrium with the present biosphere.

References

1. Park, S., Hanna, L. M., Taylor, R. T., and Droge, M. W. Biotechnology and Bioengineering (submitted).
2. Vogel, J. S., Nelson, D. E., and Southon, J. R. (1989) Radiocarbon 31, 145–149.
3. Vogel, J. S., Nelson, D. E., and Southon, J. R. (1987) Radiocarbon 29, 323–333.
4. Davis, J. C. (1989) Nucl. Instrum. Methods B40/41, 705–708.
5. Proctor, I. D. (1989) Nucl. Instrum. Methods B40/41, 727–730.

Results

Initial measurements of biological samples from $^{14}C$ tracer studies and of samples prepared in laboratories where $^{14}C$ is routinely used resulted in instrument contamination. As a result, new methods were devised involving careful handling of each sample, use of disposable labware, and isolation of samples from potential sources of gross contamination. In addition, analytical standards (ANU sugar) with each DNA sample were alternated to determine when and if contamination occurred, and water vapor was flushed through the graphitization apparatus between samples to remove any excess $^{14}C$ left from the previous sample. $^{14}C$-free acrylamide samples were also used to test for sample contamination of either the graphitization apparatus or the spectrometer. Actual measurements were made on DNA diluted with $^{14}C$-depleted carbon prior to analysis. In one case, an 18,000 Modern sample was measured directly, but no residual $^{14}C$ from this sample could be detected in any of the subsequent sample preparations and measurements (data not shown). DNA from animals given the 5 mg/kg body weight dose of MeIQx averaged a 46,000-fold enrichment in $^{14}C$ but actual measurements at this dose were below 53 Modern due to dilution of the DNA with $^{14}C$-depleted carbon. In no case did the $^{14}C$-enriched samples contaminate either the graphitizer station or the spectrometer, as determined from the lack of a statistical increase in the $^{14}C$ content of the ANU sugar or acrylamide standards.

Instrument performance was determined by accessing the variation in measurements on replicate treatments and multiple measurements on the same sample. The coefficient of variation in $^{14}C$ content and number of adducts among animals at each dose level was approximately 10% by AMS. The average within-sample coefficient of variation in $^{14}C$ content of these measurements was 2% based on multiple measurements of standard $^{14}C$-containing materials, and was 8% for multiple measurements made on separately prepared aliquots of the same DNA.

Figure 2:
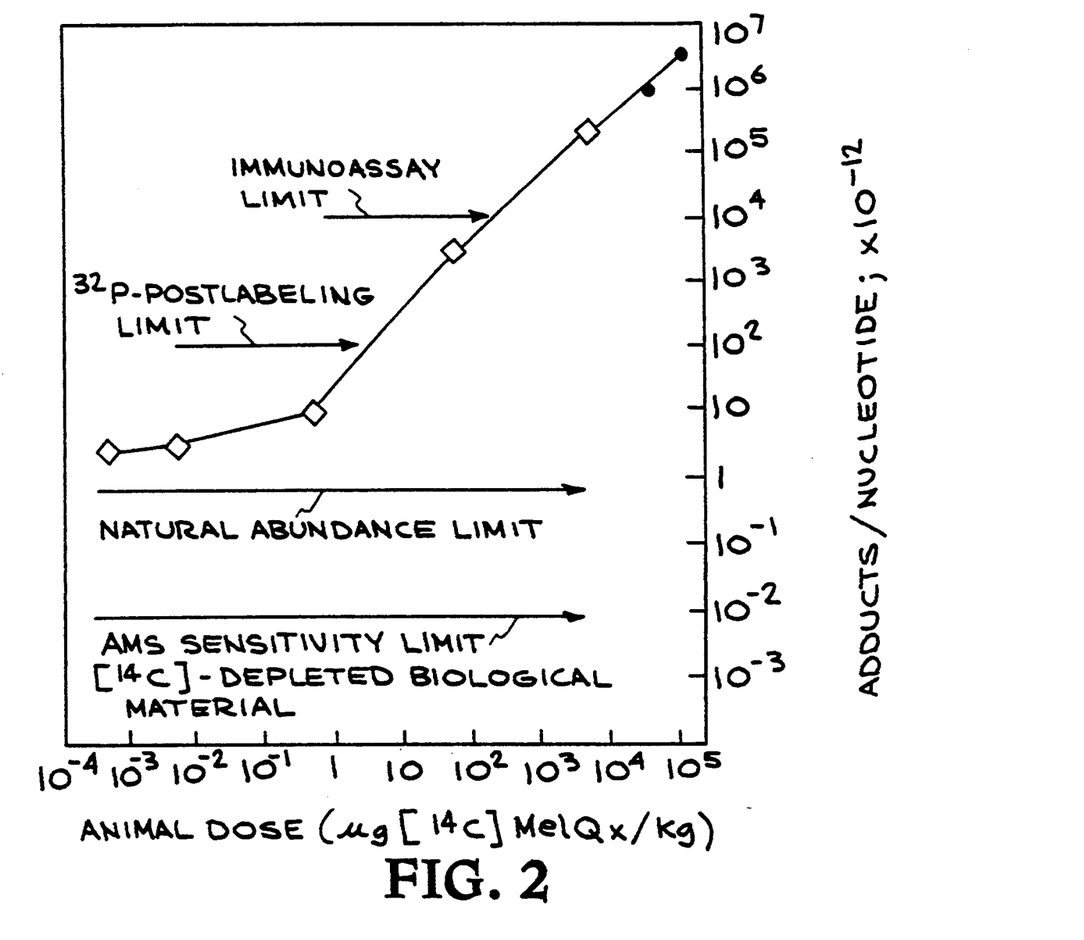
FIG. 2: Is a graph showing the effect of MeIQx exposure on DNA adduct levels found in the hepatic DNA of mice as determined by accelerator mass spectrometry (◊).

The amount of DNA analyzed in these experiments ranged from 1 μg to 1 mg. Adduct levels per $10^{12}$ nucleotides were found to be dependent (P 0.001) on dose of MeIQx administered (FIG. 2). A linear relationship existed from a dose of 500 ng/kg of body weight to a MeIQx dose of 5 mg/kg (P 0.0001). The $^{14}C$ content of the DNA of animals at the 5 ng/kg dose are not significantly elevated (P 0.10) over levels detected in unexposed animals.

Figure 3:
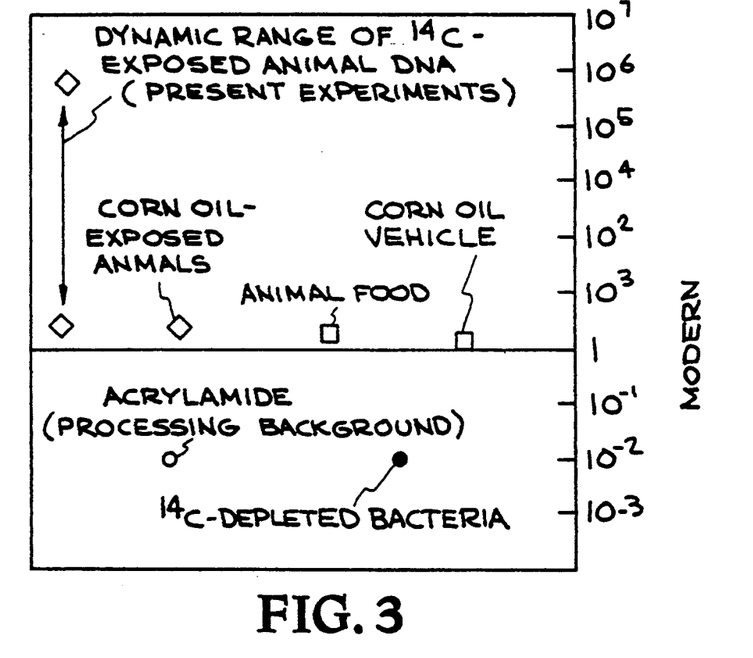
FIG. 3: Is a graph showing the $^{14}C$ content of control materials reported as fraction Modern (□, □,o) in relation to the range in values obtained for [$^{14}C$] MeIQx-exposed mice (◊).

The measured $^{14}C$ content of the DNA from control animals, animal food, and other potential sources of $^{14}C$ utilized in this study are shown in FIG. 3 in relation to the $^{14}C$ content of the dosed animals. Animal food was found to be contemporary (1.2 Modern) as was the corn oil (1.15 Modern) used to administer the MeIQx- Samples prepared from $^{14}C$-free acrylamide consistently measured were Modern. Solvents and solutions used in the study were Modern in $^{14}C$ content, but radiocarbon levels in surface swipes of work areas showed that some areas were contaminated with $^{14}C$ from previous tracer experiments. These areas ranged between 18 and 18,000 Modern (data not shown).

Figure 4:
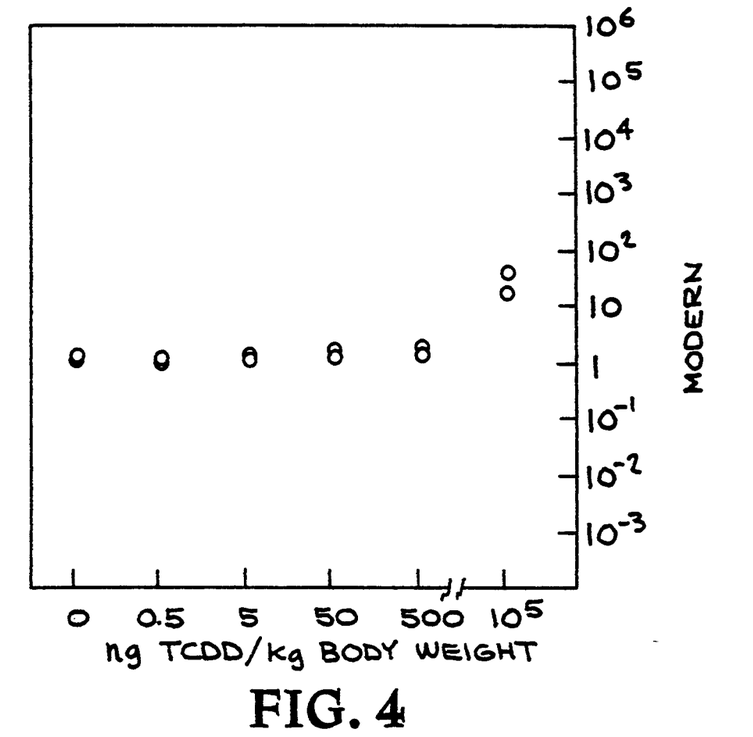
FIG. 4: Is a graph showing $^{14}C$ levels found in the DNA of [U-$^{14}C$] 2,3,7,8-tetrachlorodibenzo-p-dioxin (TCDD) exposed mice.

The extreme sensitivity of AMS for $^{14}C$ suggests that very small amounts of non-covalently bound $^{14}C$, or $^{14}C$-bound macromolecular contaminants in the DNA would be detectable, and thus could bias the adduct determinations. To evaluate this possibility and to ensure that our procedures adequately purify DNA, we measured DNA adduct formation with TCDD, a carcinogen which has not been found to covalently bind to DNA. TCDD absorption is rapid and approximately 33% of the administered dose should reach the liver tissue within the time frame of this study. These distribution kinetics are similar to that expected for MeIQx. The TCDD was uniformly labeled with $^{14}C$ (11.7 $^{14}Cs$ per molecule on average) corresponding to 10 times more $^{14}C$ at each dose level than the MeIQx-exposed animals. Hepatic DNA samples isolated from the TCDD-exposed mice (FIG. 4) were modern in $^{14}C$ content (1.06–1.7 Modern) except at the highest TCDD dose level (100 μg/kg; 14 Modern). The highest TCDD dose level is approximately the $LD_{50}$ for TCDD in mice and the significance of the higher [$^{14}C$] DNA values needs to be explored further. This data suggests that (or little) nonDNA-bound $^{14}C$ remains after our DNA purifications since all DNA samples, except those from the highest TCDD dose, were modern in $^{14}C$ content. This suggestion is supported by the fact that $^{14}C$ levels measured in DNA from the MeIQx-exposed mice ranged from 100 to 4000-fold greater than with the TCDD-exposed mice. Even at the highest TCDD dose, greater than 99.9% of the $^{14}C$ distributed to the liver was removed through our DNA purification protocol. Additionally, this result shows that animal handling and DNA isolations can be carried out without radiocarbon contamination when done using appropriate procedures.

The limiting factor for biological measurements in the detection of [$^{14}C$]-tagged molecules will be the natural abundance of $^{14}C$ existing in the biosphere. Thus, we felt utilization of [$^{14}C$]-depleted hosts would be valuable for modeling dosimetry. Towards this end, Methylosinus trichosporium was grown using petroleum-derived methane as the sole carbon source. Measurement of the $^{14}C$ content of this organism verified that the $^{14}C$ content can be easily depleted to an equivalent of 0.01 Modern which is 200 times less than our lowest mouse sample (FIG. 3).

The present detection limit for [$^{14}C$]-labeled DNA adducts by AMS is 1 adduct/$10^{11}$ nucleotides. This corresponds to a one order of magnitude improvement over the very best sensitivity offered to date by $^{32}P$-postlabeling assay. AMS provides a direct measure of the number of adducts present without relying on enzymatic recognition of adducts and/or quantitative extraction recoveries. In addition, these measurements are 3 to 5 orders of magnitude better than other techniques used for quantitative assay of DNA adducts such as ultrasensitive radioimmunoassays, surface enhanced Raman spectroscopy, gas chromatography, mass spectrometry, laser-induced phosphorescence, fluorescence spectrometry, fluorescence line narrowing spectrometry, and synchronous scanning fluorescence spectrometry. Reproducibility of the measurements is very high (within 10%) and is limited by animal to animal variation.

Instrument precision in these measurements is 2% with further improvements likely. Thus AMS is a uniquely sensitive, and reproducible technique for adduct measurement and will easily complement existing methods.

The inability to measure adducts in animals given 5 ng MeIQx/kg and less is seemingly due to contamination of the DNA during isolation and does not represent a biological threshold. It is not the result of the inability to detect modern, or lower levels of $^{14}C$. Contamination most likely occurred during animal handling and/or DNA isolation. This is evident from comparison of the expected amount of $^{14}C$ in contemporary materials to the amounts actually found in the control animals (FIG. 3). Measurement of corn oil and animal food corresponded to contemporary carbon (approximately 1.2 Modern) but control animals were 2-fold above contemporary in $^{14}C$ content. Measurement of acrylamide, and the $^{14}C$-depleted methanotrophic bacteria demonstrate the sensitivity of the carbon preparation and measurement process and that we can measure up to 100-fold below contemporary levels of $^{14}C$. Thus, the relatively high levels of $^{14}C$ found in animals not given radioisotope are due to sample contamination, and to the proximity of the total $^{14}C$ content of the samples to the ambient $^{14}C$ content of the DNA itself. Extreme care must be taken to avoid excess contamination above this natural limit.

The work station that measured a minimum of 18,000 Modern aptly demonstrates the problems encountered in preparing samples for AMS measurement in laboratories with a history of $^{14}C$ use. However, the data from the TCDD exposure study shows that with proper procedures, contamination problems and non-specific binding of $^{14}C$ can be eliminated.

Additional increases of 2 to 10-fold in the sensitivity of DNA adduct detection by AMS will be possible through contamination reduction, but will certainly be no better than that allowed by the natural abundance of $^{14}C$ in biological molecules (modern carbon from the biosphere is $1/10^{12}$ $^{14}C$). However, enhancement of sensitivity can be gained using $^{14}C$-depleted hosts. Growth of yeast and bacteria on petroleum feedstocks has been reported previously. We have grown $^{14}C$-depleted Methylosinus trichosporium on petroleum derived methane and verified that the $^{14}C$ content can be easily depleted to an equivalent of 0.01 Modern, demonstrating a potential 100-fold increase in sensitivity. Such model organisms could be of use in studying the consequences of dose on the metabolism, kinetics, and effects of xenobiotic exposures. Growth of other hosts on petroleum based foodstuffs should result in similarly low radiocarbon backgrounds.

Clinical applications and research using human subjects can be envisioned with AMS radioisotope tracing. The detection sensitivity and small sample size requirements of AMS make it ideal for measurements of small quantities of easily accessible human cells, in addition to the liver tissue demonstrated here. Therapeutic parameters for individuals could be determined by AMS through administration of small dosages of $^{14}C$-labeled pharmaceuticals. Such custom tailoring of effective therapeutic regimens would be particularly valuable for cancer chemotherapy as the extremely small human radiation dose from the drug would not be an issue. The estimated effective [$^{14}C$]-MeIQx radiation dose equivalent in this study, based on a 24 hr biological half-life, corresponded to 0.003 milliSieverts at the 500 ng/kg dose level. This exposure is approximately 0.1% of the total annual adult exposure to ionizing radiation from known natural sources. Mutagen exposure, in such protocols, becomes a more significant issue than the radiation dose incurred.

Use of AMS in the present measurements of low-level DNA adducts provides no structural information on adduct type. Such information is better obtained with the postlabeling assay. However, molecular information on adduct type should be obtainable with AMS when it is used in conjunction with appropriate techniques to purify and separate adducts prior to measuring the $^{14}C$ ratios. The need for use of radiolabeled compounds with AMS is a limitation, but radiation exposure, due to the extreme sensitivity of the technique, is significant, particularly when used in the laboratory and clinical setting where very low levels of isotopically-tagged compounds are measured. AMS also has the advantage of measuring these low $^{14}C$ levels in small samples. Utilization of rare stable isotopes seems possible as well. Thus AMS will be useful in any application where sensitivity of detection is limiting.

The present results with DNA adduct dosimetry demonstrate the utility of AMS for quantitive measurement of low-frequency biomolecular events following exposure to small concentrations of $^{14}C$-labeled xenobiotics. The technique will be useful in clinical and laboratory environments where sensitivity of detection is not possible by other assays and in a wide number of applications beyond the adduct detection reported here. The technique has a dynamic range covering many orders of magnitude, is reproducible, sensitive, and $^{14}C$ contamination is controllable. Furthermore, requirements for $^{14}C$ enrichment are 5-6 orders of magnitude below traditional decay counting methods. Other candidate isotopes for low-level biomedical and environmental dosimetry applications are $^{3}H$ and $^{41}Ca$. These potential new applications, coupled with the $^{14}C$ measurements reported here, show AMS technology to be an important new tool for the biomedical and environmental sciences community.

Other long-lived isotopes which are suitable for use in the process of this invention include $^{26}Al$, $^{36}Cl$, $^{79}Se$, and $^{129}I$.

In addition to the details of and methods for sample handling which are set forth herein and form a part of the invention, specific details for preparing samples for AMS analysis are set forth in co-pending application Ser. No. 07/555,080, filed Jul. 13, 1990 concurrently herewith, entitled "Method of Measurement In Biological Systems, Turteltaub et al., applicants' file No. IL-8567B, all of which is incorporated herein by reference.

Applications of highly specific and sensitive measurements of molecular interactions are numerous in the fields of environmental detection and remediation, biomolecular research, and low-level chemical dosimetry. The latter field includes the possibility of direct drug titration in human chemotherapy for cancer and other ailments.

The foregoing description of preferred embodiments of the invention have been presented for purposes of illustration and description. It is not intended to be exhaustive or to limit the invention to the precise forms disclosed, and obviously many modifications and variations are possible in light of the above teachings. The embodiments were chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto and their equivalents.

We claim:

1. A method for detection of long-lived radioisotopes in small biochemical samples, comprising:
   a. selecting a biological host in which selected radioisotopes are present at a concentration equal to or less than the concentration in the ambient biosphere,
   b. preparing a long-lived radioisotope-labeled chemical specie, c. administering said chemical specie to said biological host in one or more doses that do not cause either significant damage to the host's biological system or a significant increase in radiological exposure to the host over the ambient radiation environment or from natural internal sources of radiation, d. allowing dissemination and reaction of said chemical specie with said biological system of said host, e. isolating a reacted fraction of a biological substance from said host in a manner sufficient to avoid contamination of the fraction from extraneous sources of the radioisotope, f. converting said fraction of biological substance to a solid, inert, non-volatile, thermally conductive inorganic sample which efficiently produces charged ions in an ion source without introduction of significant isotopic fractionation, and g. measuring the radioisotope concentration in the inorganic sample using an accelerator mass spectrometer.

2. The method as recited in claim 1, wherein step (c) comprises:

administering doses to the host with the labeled chemical specie in order of radioisotope activity, from lowest to highest.

* * * * *